(12) United States Patent
Malberg et al.

(10) Patent No.: US 8,986,384 B2
(45) Date of Patent: Mar. 24, 2015

(54) METHOD FOR STABILIZING SPINE

(71) Applicants: Marc I. Malberg, Princeton, NJ (US); Gretchen Dougherty Shah, Wayne, NJ (US); Rul J Ferreira, Livingston, NJ (US)

(72) Inventors: Marc I. Malberg, Princeton, NJ (US); Gretchen Dougherty Shah, Wayne, NJ (US); Rul J Ferreira, Livingston, NJ (US)

(73) Assignee: ResSpond Spinal Systems, Princeton, NJ (US)

( * ) Notice: Subject to any disclaimer, the term of this patent is extended or adjusted under 35 U.S.C. 154(b) by 32 days.

(21) Appl. No.: 13/751,733

(22) Filed: Jan. 28, 2013

(65) Prior Publication Data

US 2013/0190878 A1     Jul. 25, 2013

Related U.S. Application Data

(63) Continuation-in-part of application No. 12/206,015, filed on Sep. 8, 2008, now Pat. No. 8,361,148, which is a continuation of application No. 11/697,322, filed on Apr. 6, 2007, now Pat. No. 7,465,317, which is a continuation of application No. 10/897,371, filed on Jul. 22, 2004, now Pat. No. 7,318,839.

(60) Provisional application No. 60/489,731, filed on Jul. 23, 2003.

(51) Int. Cl.
*A61F 2/44* (2006.01)
*A61F 2/30* (2006.01)
(Continued)

(52) U.S. Cl.
CPC ....... *A61F 2/442* (2013.01); *A61F 2002/30772* (2013.01); *A61F 2002/4629* (2013.01); *A61F 2/4455* (2013.01); *A61F 2220/0025* (2013.01); *A61F 2002/30505* (2013.01); *A61F 2230/0058* (2013.01); *A61F 2250/0006* (2013.01); *A61F 2002/448* (2013.01); *A61F 2002/30433* (2013.01); *A61F 2002/30579* (2013.01); *A61F 2310/00023* (2013.01); *A61F 2310/00359* (2013.01); *A61F 2220/0091* (2013.01); *A61F 2002/30616* (2013.01); *A61F 2002/30507* (2013.01); *A61F 2220/0041* (2013.01); *A61F 2002/30179* (2013.01);
(Continued)

(58) Field of Classification Search
CPC ............ A61F 2/44; A61F 2002/30179; A61F 2002/30507; A61F 2002/3051; A61F 2002/30525; A61F 2002/30579
USPC ................................ 623/17.11, 17.15, 17.16
See application file for complete search history.

(56) References Cited

U.S. PATENT DOCUMENTS

| 5,192,327 A | 3/1993 | Brantigan |
| 5,397,364 A | 3/1995 | Kozak et al. |

(Continued)

FOREIGN PATENT DOCUMENTS

| FR | 2717068 | 9/1995 |
| WO | 0025706 | 5/2000 |

(Continued)

*Primary Examiner* — Bruce E Snow
(74) *Attorney, Agent, or Firm* — Law Offices of Robert F. Zielinski LLC

(57) ABSTRACT

A method of stabilizing a portion of a spine includes pivoting first and second members of an expandable spinal implant relative to one another to a closed configuration in which the spinal implant has a compact profile, inserting the spinal implant in the closed configuration into the spine between first and second vertebral bodies, and pivoting and locking the first and second members crosswise to an expanded configuration while the spinal implant is within the spine. The first and second members are separate from and coupled to one another.

11 Claims, 13 Drawing Sheets

(51) Int. Cl.
*A61F 2/46* (2006.01)
*A61F 2/28* (2006.01)

(52) U.S. Cl.
CPC .................. *A61F 2002/30471* (2013.01); *A61F 2002/30538* (2013.01); *A61F 2/28* (2013.01); *A61F 2002/30975* (2013.01); *A61F 2002/30846* (2013.01); *A61F 2002/30476* (2013.01)
USPC ..................................................... 623/17.11

(56) References Cited

U.S. PATENT DOCUMENTS

| | | | |
|---|---|---|---|
| 5,554,191 | A | 9/1996 | Lahille et al. |
| 5,658,337 | A | 8/1997 | Kohrs et al. |
| 5,865,848 | A | 2/1999 | Baker |
| 6,039,761 | A | 3/2000 | Li et al. |
| 6,045,579 | A | 4/2000 | Hochshuler et al. |
| 6,126,689 | A | 10/2000 | Brett |
| 6,159,211 | A | 12/2000 | Boriani et al. |
| 6,159,245 | A | 12/2000 | Meriwether et al. |
| 6,179,873 | B1 | 1/2001 | Zientek et al. |
| 6,179,875 | B1 | 1/2001 | Von Strempel et al. |
| 6,190,414 | B1 | 2/2001 | Young et al. |
| 6,193,757 | B1 | 2/2001 | Foley et al. |
| 6,210,442 | B1 | 4/2001 | Wing et al. |
| 6,241,769 | B1 | 6/2001 | Nicholson et al. |
| 6,251,140 | B1 | 6/2001 | Marino et al. |
| 6,454,807 | B1 | 9/2002 | Jackson |
| 6,488,710 | B2 | 12/2002 | Besselink et al. |
| 6,743,255 | B2 | 6/2004 | Ferree |
| 7,087,055 | B2 * | 8/2006 | Lim et al. ............ 606/99 |
| 7,318,839 | B2 | 1/2008 | Malberg et al. |
| 8,062,373 | B2 * | 11/2011 | Fabian, Jr. ............ 623/17.16 |
| 2002/0082693 | A1 | 6/2002 | Ahlgren |
| 2004/0254643 | A1 | 12/2004 | Jackson |
| 2007/0073398 | A1 | 3/2007 | Fabian et al. |

FOREIGN PATENT DOCUMENTS

| | | |
|---|---|---|
| WO | 010895 | 1/2001 |
| WO | 0205733 | 1/2002 |
| WO | 2007040708 | 4/2007 |

\* cited by examiner

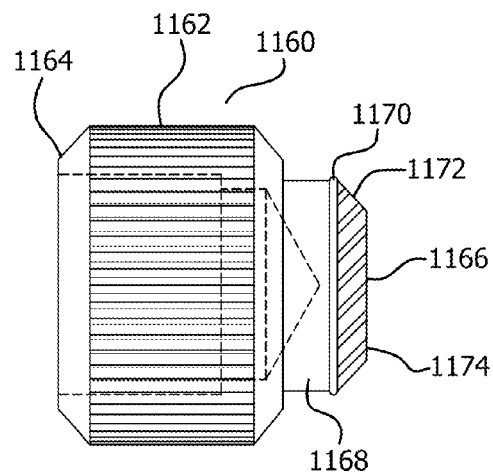
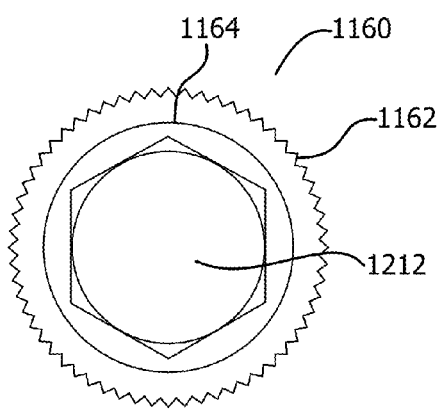
FIG. 18   FIG. 19
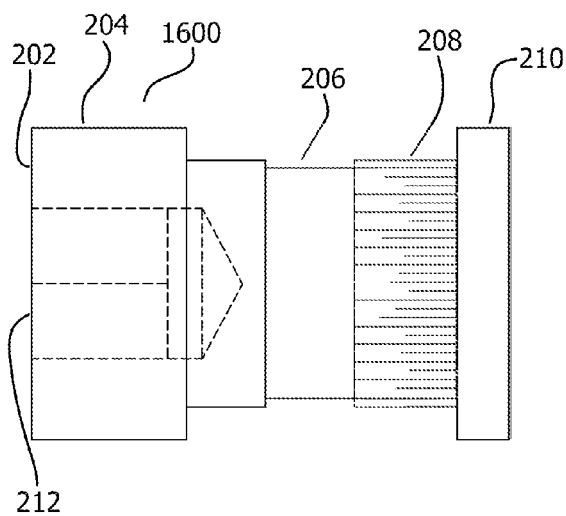
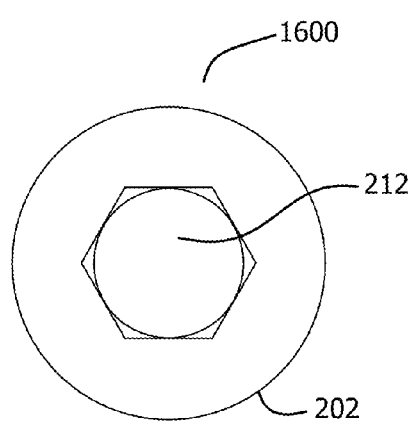
FIG. 20   FIG. 21

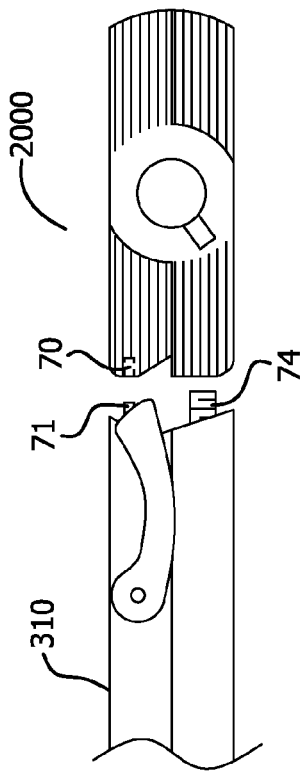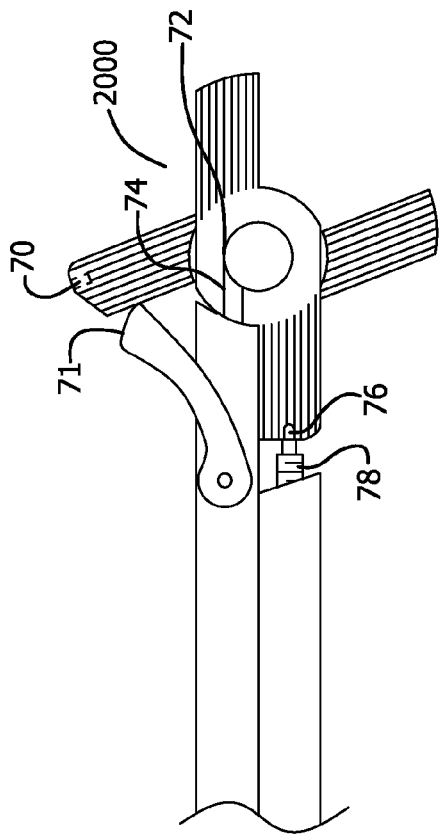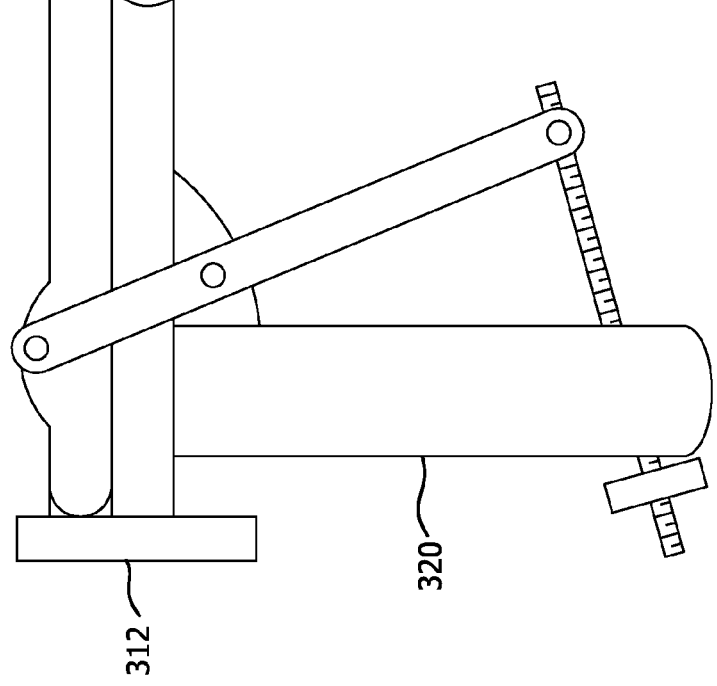

METHOD FOR STABILIZING SPINE

CROSS-REFERENCE TO RELATED APPLICATIONS

This application is a continuation-in-part of U.S. patent application Ser. No. 12/206,015, filed on Sep. 8, 2008 issued as U.S. Pat. No. 8,361,148 on Jan. 29, 2013 which is a continuation of Ser. No. 11/697,322 filed on Apr. 6, 2007 issued as U.S. Pat. No. 7,465,317 on Dec. 16, 2008, which is a continuation of U.S. patent application Ser. No. 10/897,371 filed on Jul. 22, 2004, issued as U.S. Pat. No. 7,318,839 on Jan. 15, 2008, which claims the benefit of U.S. Provisional Application Ser. No. 60/489,731 filed on Jul. 23, 2003. The disclosures of the above applications are incorporated herein by reference.

INTRODUCTION

The spinal column is a highly complex structure which houses and protects critical elements of the nervous system. In spite of these complexities, the spinal column is a highly flexible structure, capable of a high degree of curvature and twist through a wide range motion. Genetic or developmental irregularities, trauma, chronic stress, tumors, and disease, however, can result in spinal pathologies which either limit this range of motion, or threaten the critical elements of the nervous system housed within the spinal column.

In various orthopedic surgical procedures, it is necessary to stabilize portions of a spinal column relative to one another. This need is typically a result of disease, damage or congenital deformation. In one method of treatment for intervertebral disk degeneration, the normal gap between adjacent vertebral bodies is surgically re-established and maintained with a rigid spacer inserted between the bodies. The rigid spacer is filled with bone graft material to facilitate bony fusion of the two vertebral bodies. A successful fusion stabilizes the spine, reduces pressure on the spinal cord and nerve roots, and reduces or eliminates back pain.

While known devices for spinal fusion have proven to be effective in various applications, there remains a need for spinal implants that do not require large incisions for implantation, that can relieve localized stress on adjacent vertebral end plates, and that can prevent migration and retropulsion within the spinal column.

SUMMARY

The present teachings provide an expandable spinal implant including a first member and a second member. The first member has first and second arms. The first and second arms of the first member both including an upper face partially defining an upper contact area of the implant and a lower face partially defining a lower contact surface of the implant. The second member has first and second arms that both include an upper face partially defining an upper contact area of the implant and a lower face partially defining a lower contact surface of the implant. The first and second members are pivotally coupled to each other for relative movement about a rotation axis between a closed position for inserting the implant into a spine and an expanded position for providing structural support to the spine. The rotation axis extends generally perpendicular to the upper and lower contact surfaces.

The present teachings also provide an expandable spinal implant having first and second members both with a central portion and first and second arms extending from the central portion. The central portion of the second member is coupled to the central portion of the first member for rotation about a rotation axis between a closed orientation for insertion into a spine and an expanded orientation for providing structural support to the spine. The spinal implant further includes a locking mechanism for arresting relative movement between the first member and the second member.

The present teachings provide a method of stabilizing a portion of a spine. The method includes providing a spinal implant having a first elongated member and a second elongated member. The first elongated member has a central portion rotatably coupled to a central portion of the second elongated member for rotation between a closed position and an expanded position. The method additionally includes orienting the first and second elongated members in the closed position and inserting the spinal implant into the spine between first and second vertebral bodies. The rotation axis is vertically oriented. The method further includes rotating the first and second elongated members to the expanded position while the spinal implant is within the spine.

The present teachings further provide an expandable spinal implant that includes a first member having first and second arms and a central portion between the first and second arms, and a second member completely separate from the first member, the second member having first and second arms and a central portion between the first and second arms. The central portion of the first member is rotatably coupled to the central portion of the second member about a rotation axis substantially perpendicular to the central portions between a closed position for inserting the implant into a spine and an expanded position for providing structural support to the spine, the first and second members coupled to each other such that the first and second arms of the first member alternate with the first and second arms of the second member.

The present teachings provide an expandable spinal implant that includes a first member having a central portion and first and second arms extending from the central portion of the first member, a second member having a central portion and first and second arms extending from the central portion of the second member, the central portion of the second member coupled to the central portion of the first member for rotation about a rotation axis between a closed orientation for insertion into a spine and an expanded orientation for providing structural support to the spine, and a locking mechanism for arresting relative movement between the first member and the second member, the locking mechanism including a locking member manually operable to engage the first member with the second member in the expanded orientation.

The present teachings further provide an expandable spinal implant that includes a first member having a central portion and first and second arms extending from the central portion of the first member, a second member having a central portion and first and second arms extending from the central portion of the second member, and a pivot and locking member engaging respective first and second openings of the central portions of the first and second members for rotation between a closed orientation for insertion of the spinal implant into a spine and an expanded orientation for providing structural support to the spine.

The present teachings further provide a method of stabilizing a portion of a spine. The method includes pivoting first and second members of an expandable spinal implant relative to one another to a closed configuration in which the spinal implant has a compact profile, inserting the spinal implant in the closed configuration into the spine between first and second vertebral bodies, and pivoting the first and second members crosswise to an expanded configuration while the spinal implant is within the spine. The first and second members are separate from and coupled to one another.

In another aspect, the method includes pivoting first and second members of an expandable spinal implant relative to one another to a closed configuration in which the spinal implant has a compact profile and inserting the spinal implant in the closed configuration into the spine between first and second vertebral bodies. The first and second members are separate from and coupled to one another. The method further includes pivoting and locking the first and second members to an expanded configuration while the spinal implant is within the spine, and arresting a relative movement between the first and second members by operation pivot and locking gear operatively connected to the first and second central portions of the first and second members.

In a further aspect, the method includes inserting an expandable spinal implant in a closed configuration between first and second vertebral bodies of a spine, and pivoting and locking first and second members of the expandable implant to an expanded configuration while the spinal implant is within the spine. The first and second members are separate from and coupled to one another. The method further includes rotating a threaded pivot and locking gear received in the central portions of the first and second members which is positioned between the first and/or second members, and locking the first and second elongated members in the expanded configuration with the threaded fastener received within the central portion.

In yet another aspect, and pivoting the first and second members from a closed to an open position by means of a special tool and then locking the members in relative position to one another by insertion of locking pin or threaded fastener positioned with the central portion. Further areas of applicability of the present teachings will become apparent from the detailed description provided hereinafter. It should be understood that the detailed description and specific examples are intended for purposes of illustration only and are not intended to limit the scope of the present teachings.

BRIEF DESCRIPTION OF THE DRAWINGS

The present teachings will become more fully understood from the detailed description and the accompanying drawings, wherein:

FIG. 18 is a side view of one embodiment of a pivot and locking gear of the expandable spinal implant of FIGS. 11 through 17;

FIG. 19 is an end view of one embodiment of a pivot and locking gear of the expandable spinal implant of FIGS. 11 through 17;

FIG. 20 is a side view of one embodiment of a pivot and locking gear of the expandable spinal implant of FIGS. 1 through 10;

FIG. 21 is an end view of one embodiment of a pivot and locking gear of the expandable spinal implant of FIGS. 1 through 10;

FIG. 25 is a partial side view of an exemplary adjustment tool for used in combination with an embodiment of a expandable spinal implant of the present invention as shown in FIGS. 22 through 23

FIG. 26 is a partial side view of the adjustment tool of FIG. 25 shown in operative engagement with an expandable spinal implant of the present invention.

DESCRIPTION

The following description of various embodiments is merely exemplary in nature and is in no way intended to limit the present teachings, applications, or uses.

Figure 1:
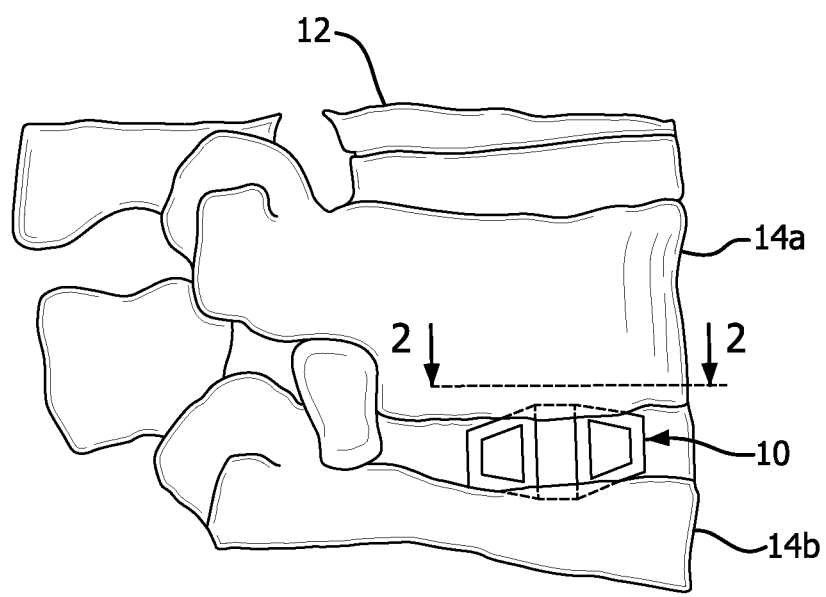
FIG. 1 is a side view of an embodiment of an expandable spinal implant constructed in accordance with the present teachings, the expandable spinal implant shown operatively positioned between vertebral bodies of a human spine.
Figure 2:
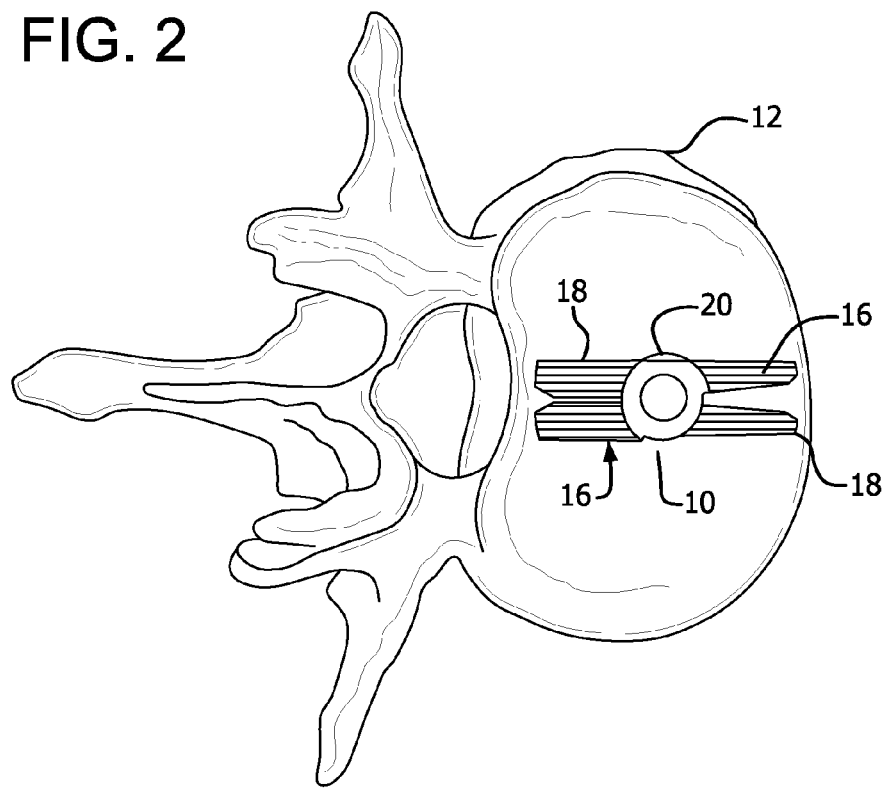
FIG. 2 is a cross-sectional view taken along the line 2-2 of FIG. 1, the expandable spinal implant shown in a contracted or closed condition to facilitate insertion into the spine.
Figure 3:
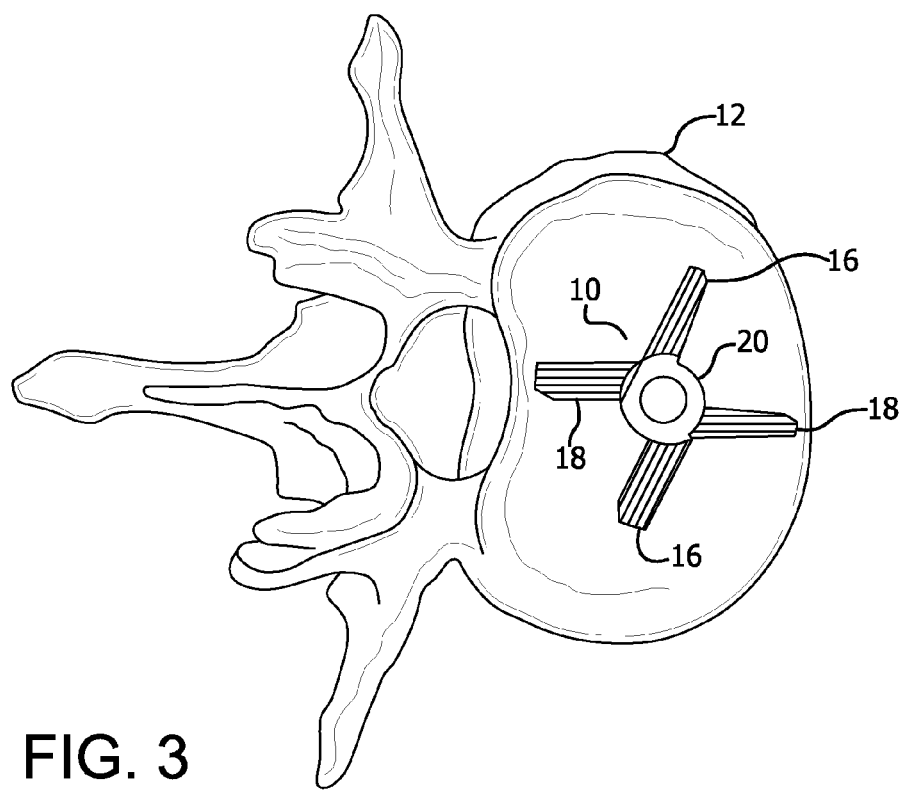
FIG. 3 is a cross-sectional view similar to FIG. 2, the expandable spinal implant shown in an expanded or open condition in the spinal space.

With initial reference to FIG. 1 and FIG. 2, an exemplary spinal implant constructed in accordance with the present teachings is illustrated and generally identified at reference number 10. The spinal implant 10 is shown operatively associated with a human spinal column 12. More specifically, the spinal implant 10 is shown positioned between a first vertebra 14a and a second vertebra 14b to stabilize the spine 12.

With continued reference to the environmental views of FIGS. 1 and 2 and additional reference to FIGS. 3 through 10, the spinal implant 10 of the present teachings will be addressed in detail. The spinal implant 10 is illustrated to generally include a first member or first elongated member 16 and a second member or second elongated member 18. As will become more apparent below, the first elongated member 16 and the second elongated member 18 are completely separate members and are coupled to one another for relative movement between a closed position or orientation (shown in FIG. 2) and an expanded position or orientation (shown in FIG. 3). As will be appreciated more fully below, the closed orientation facilitates insertion of the spinal implant 10 within the spine 12 through a small incision, while the expanded orientation disperses the load on the adjacent end plates.

Figure 4:
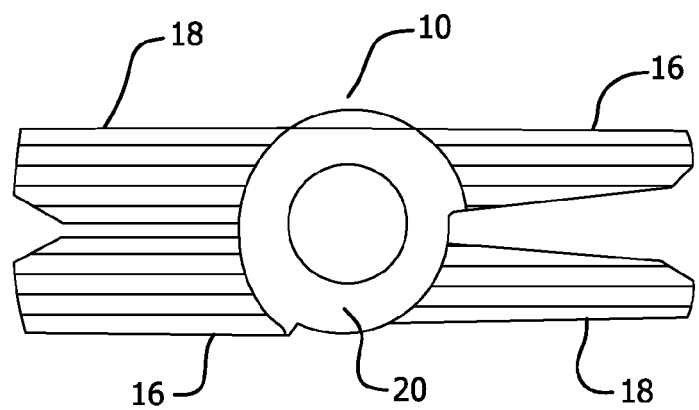
FIG. 4 is a top perspective view of the expandable spinal implant of FIG. 2 shown outside the spinal space for purposes of illustration.
Figure 5:
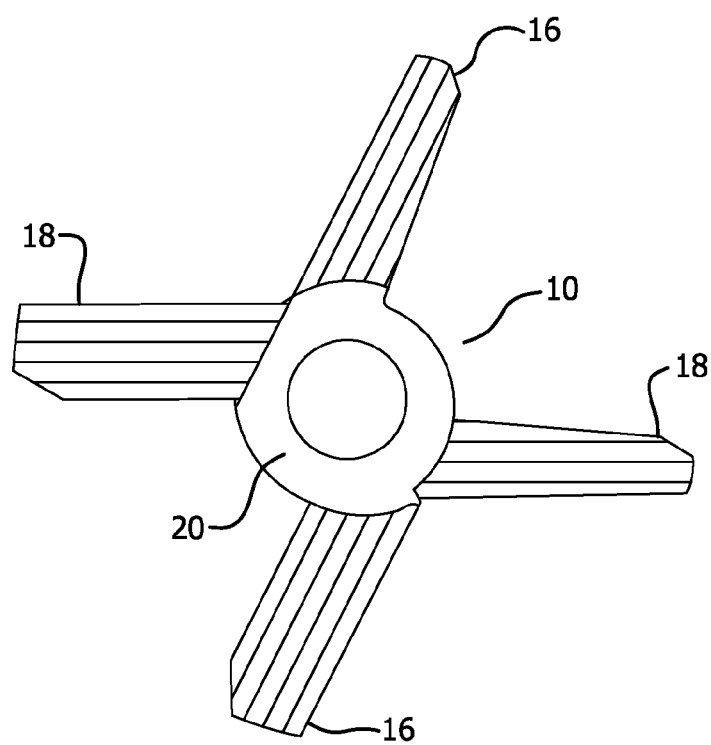
FIG. 5 is a top perspective view of the expandable spinal implant of FIG. 3 shown outside the spinal space for purposes of illustration.
Figure 6A:
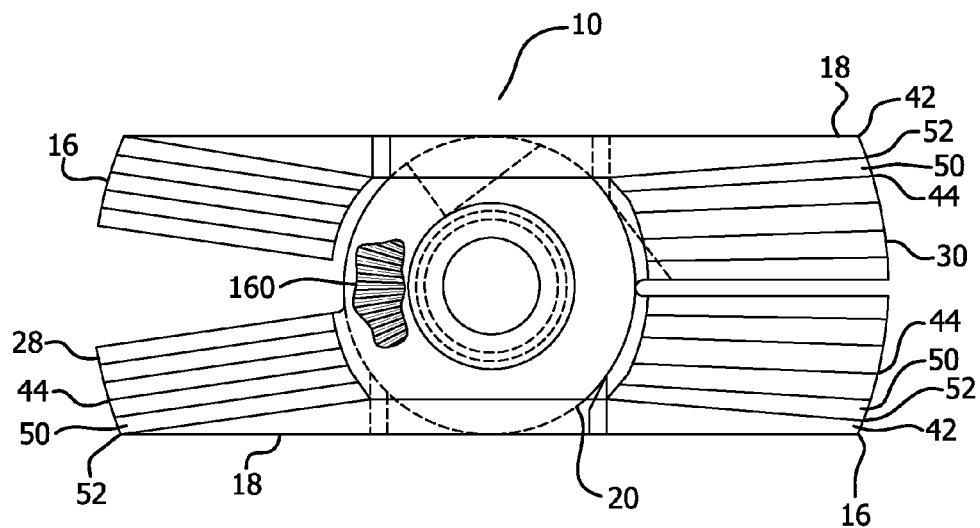
FIG. 6A is a partial cut away top plan view of an expandable spinal implant according to the present teachings, and shown removed from the spine for purposes of illustration.
Figure 6B:
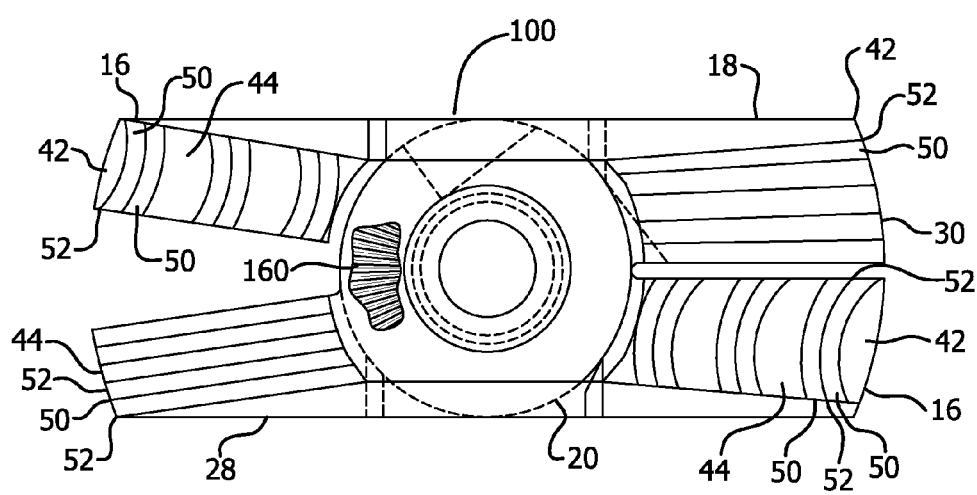
FIG. 6B is a partial cutaway top plan view of an alternate version of a expandable spinal implant according to the present teachings, and shown removed from the spine for purposes of illustration.
Figure 7A:
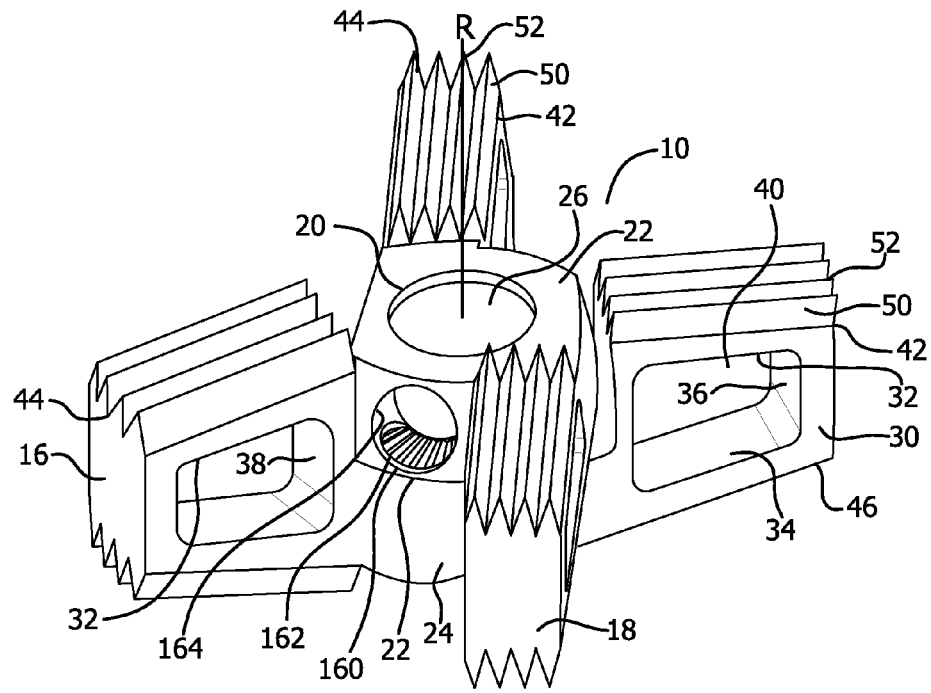
FIG. 7A is a perspective view of an expandable spinal implant according to the present teachings, and shown removed from the spine for purposes of illustration.
Figure 7B:
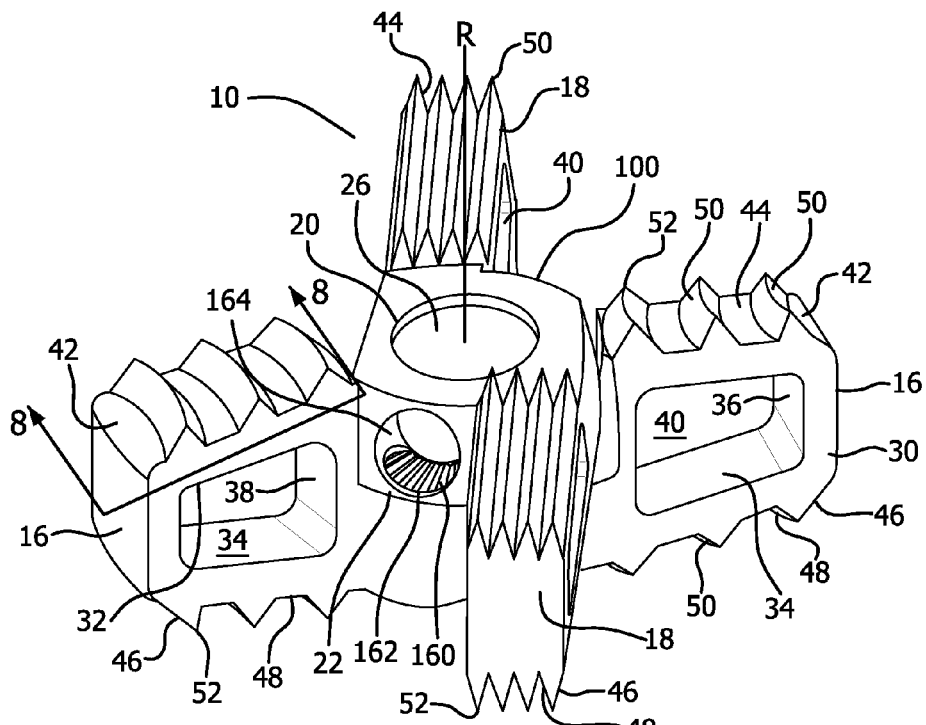
FIG. 7B is a perspective view of an alternate version of an expandable spinal implant according to the present teachings, shown removed from the spine for purposes of illustration.

With particular reference to FIGS. 4, 5, 6A and 6B, implant 10 and 100 are shown removed from the spine 12 for purposes of illustration and articulated to the open position. As shown in FIGS. 4 and 5, the first elongated member 16 and the second elongated member 18 can be substantially similar in dimension and structure to each other but need not be exactly, as is shown in FIGS. 6A and 6B. For this reason, a description of the first elongated member 16 will serve to fully describe both the first elongated member 16 and the second elongated member 18 for exemplary implants 10 and 100. As used throughout this disclosure, similar structures and elements will share like reference numbers. Thus, reference numbers for implant 10 will be used throughout the disclosure as will be referenced in FIGS. 1-10, FIGS. 14A, 14B, 16, 17, 22, 23 and 24 and in other Figures. Common elements of the first elongated member 16 and the second elongated member 18 will be identified accordingly. It will be appreciated, however, that the first and second elongated members need not be substantially identical, as is illustrated in FIGS. 6B and 7B and for another exemplary implant 100, 1000 and 2000 respectively described below.

Various different views of the first elongated member 16 are provided in FIGS. 4 though 7 in which the first elongated member 16 is separated from the second elongated member 18. With specific reference to FIGS. 6A, 6B, 7A and 7B, embodiments as shown having protrusions 52 oriented both radially and diagonally as will be discussed more fully below. As seen in FIGS. 7A and 7B, the first elongated member 16 is illustrated to include a central or intermediate portion 20. The central portion 20 is generally circular and upwardly extends from a lower surface of the implant. The central portion 20 has a height equal to approximately one-half the height of the implant 10. As a result, an upper or inner surface 22 of the central portion 20 is disposed at approximately a horizontal mid-line of the implant 10. The central portion 20 also includes a lower or outer surface 24.

Extending into the central portion 20, between the upper surface 22 and the lower surface 24, is recess 26. The recess 26 permits additional bone ingrowth into the implant 10 to more rigidly secure the implant 10 within the spine 12. The recess 26 may also extend deeply into the central portion and may, on some embodiments extend through the central portion 20. It will be appreciated that by extending recess completely through the central portion, the weight of the implant 10 is reduced while maintaining the strength of the implant 10. Further, the recess 26 allows the implant 10 to be easily held and positioned by a physician using suitable medical instrumentation.

Extending from opposite sides of the central portion 20 on first elongated member 18 are a first arm 28 and a second arm 30. In the embodiment illustrated in FIGS. 6A and 7A, the first arm 28 and the second arm 30 are generally extend tangentially from the central portion 20. The first arm 28 and the second arm 30 preferably extend from the central portion 20 substantially parallel to each other, but are slightly offset from each other. As seen best in FIGS. 7A and 7B, the first arm 28 and the second arm 30 each include an upper wall 32, a lower wall 34, an outer wall 36, and an inner wall 38. The inner wall 38 extends from the lower surface 24 of the central portion 20 to a distance that is roughly twice the distance between the upper surface 22 and the lower surface 24 to accommodate the central portion 20 of the second elongated member 18, as described below. In this regard, a cavity is effectively defined to receive the central portion 20 of the second elongated portion 18.

As seen most clearly in FIGS. 7A and 7B, within both the first arm 28 and the second arm 30 is a center opening or window 40. The window 40 is defined by the upper wall 32, the lower wall 34, the outer wall 36, and the inner wall 38. The window 40 reduces the weight of the implant 10 and permits bone ingrowth through the first arm 28 and the second arm 30 to better secure the implant 10 within the spine 12. Bone graft material may be placed into the intraspinal space as well as. Windows 40 further allow distribution of bone graft throughout the disc space. Referring specifically to FIGS. 7A and 7B, there is shown positioned within second elongated member 18, and upper surface of central portion 22, pivot and lock aperture 164. Pivot and lock aperture 164 provides access to pivot and locking gear teeth 160 via pivot gear aperture 162. Pivot and locking gear teeth 160 are formed on the upper surface of the lower surface of central portion 24 (as is shown more clearly with reference to FIG. 10). Upon insertion of a pivot and lock gear (as shown in FIGS. 20 and 21), and by manipulation of the pivot and locking gear with the appropriate tool, the first elongated member 16 and second elongated member 18 may be moved relative to one another from the closed position to an open position. Pivot and locking gear may include complimentary gearing to mate with pivot and locking gear teeth 160 and may further include a semi-elastic detent, annular rim or other detail including biocompatible adhesive materials and compressive or snap-fitments which facilitate permanent or semi-permanent fixing of the spinal insert 10 and 100 in the preferred position to support the vertebral segments most effectively.

The upper wall 32 includes an upper face 42 that partially defines an upper contact surface 44. The lower wall 34 includes a lower face 46 that partially defines a lower contact surface 48. As can be seen in the FIGS. 6A and 7A, upper central surfaces 44 and lower contact surface 48 extend radially from central portion 20. In these embodiments, the teeth sidewalls 50 and protrusions 52 are arranged so that the orientation of teeth sidewalls 50, protrusions 52, recess 54, recess sidewalls 56 and retention surfaces 58 of the first and second arm, relatively speaking extend away from central portion 20 in a substantially linear radial fashion (i.e perpendicular to the axis of rotation). The upper contact surface 44 and the lower contact surface 48 likewise extend radially.

Alternatively, as is shown in FIGS. 6B and 7B of at least one (or both) elongated members may have teeth sidewalls 50, protrusions 52, recesses 54, recess sidewalls and retention surfaces 58 arranged more or less diagonally (i.e. neither radially nor circumferentially) and may be flat or conically shaped. It will be understood that the upper and lower contact surfaces 44 and 48 may be likewise flat or conically shaped.

Both the upper contact surface 44 and the lower contact surface 48 are preferably formed to include a plurality of teeth 50. As is shown in FIGS. 6B and 7B, teeth 50 may extend away from the central portion 20 may be arranged more or less diagonally with the radius of curvature towards central portion 20. When the implant 10 is in its expanded orientation (as shown in FIG. 7A, for example), the teeth 50 of the various arms 28 and 30 of the implant 10 are radially arranged. In FIGS. 6B and 7B, it will be appreciated that some or all of teeth 50 (and associated structures) may be radially, diagonally and/or circumferentially arranged. Further, as seen most clearly in FIGS. 6B and 7B, teeth 50 may also be ramped or angled away from central portion 20 for more effective securing of concaved implant further within the spine 12. The ramped teeth 50 function to prevent the implant 10 from migrating and prevent retropulsion from the spine.

With particular reference to FIGS. 6A, 6B, 7A and 7B, the coupling of the first elongated member 16 with the second elongated member 18 will now be described. The first elongated member 16 and the second elongated member 18 are coupled such that the inner surface 22 of the first member 16 and the inner surface 22 of the second member 18 are in contact with each other. Further, the first arm 28 and the second arm 30 of the first elongated member 16 are each positioned between the first arm 28 and the second arm 30 of the second elongated member 18 such that the arms 28 and 30 of the first elongated member 16 alternate with the arms 28 and 30 of the second elongated member 18.

The first member 16 and the second member 18 are pivotally coupled to each other for relative movement about a rotation axis R (identified in FIGS. 7A and 7B). The rotation axis R extends through the central portion 20, generally perpendicular to the upper contact surface 44 and the lower contact surface 48. The pivotal coupling permits relative rotation of the first member 16 and the second member 18 between the closed position and the open position by means of a pivot and locking pin further described herein. The first member 16 and the second member 18 are typically rotated between the closed position and the open position by a surgeon using appropriate operating room instrumentation.

The elongated members 16 and 18 are illustrated coupled together in the closed position in FIGS. 6A and 6B. In the closed position, the first arm 28 of the first elongated member 16 is positioned roughly parallel to and adjacent to the second arm 30 of the second elongated member 18. Further, the second arm 30 of the first member 16 is positioned roughly parallel to and adjacent to the first arm 28 of the second elongated member 18. Positioning the arms 28 and 30 of the first elongated member 16 roughly parallel to and adjacent to the arms 28 and 30 of the second elongated member 18 provides the implant 10 with a slim and compact profile that permits the implant 10 to be easily inserted within the spine 12 requiring only a minimal disruption of the vertebrae 14 and the annulus (not shown). With respect to FIGS. 6A and 6B, it will be appreciated that there is a slight gap between one side of the first and second members. This is to accommodate access to one embodiment of a pivot and locking gear (discussed in FIGS. 20 and 21) positioned within pivot and lock aperture 164 shown more clearly in FIGS. 7A and 7B.

With particular reference to FIGS. 7A and 7B, the first elongated member 16 and the second elongated member 18 are shown coupled together in the open position. In the open position the first arm 28 of the first elongated member 16 is positioned apart from and in a non-parallel relationship to the second arm 30 of the second elongated member 18. Likewise, the second arm 30 of the first member 16 is positioned apart from and in a non-parallel relationship to the first arm 28 of the second elongated member 18. Generally, in the open position the first member 16 and the second member 18 are rotated such that the arms 28 and 30 of the first member 16 and the arms 28 and 30 of the second member 18 have an overall configuration approximating that of an "X". This "X" shaped configuration provides the implant 10 with a great deal of strength to support the vertebrae 14 of the spine 12.

The first elongated member 16 and the second elongated member 18 each further comprise a pair of protrusions and a pair cooperating of recesses. The protrusions extend from the upper face and the recesses are located within the outer surface 24 of the central portion 20. The recesses have a sidewall and a retention surface. As the first and second elongated members 16 and 18 are rotated from the closed position to the open position, the protrusions rotate within the recesses such that each protrusion contacts both the sidewall and the retention surface.

As seen most clearly in FIG. 7A and FIG. 7B, cooperation between the protrusions of the first elongated member 16 and the recesses of the second elongated member 18, as well as cooperation between the protrusions of the second elongated member 18 and the recesses of the first elongated member 16, ensures that the first elongated member 16 stays coupled to the second elongated member 18 when the implant 10 is in the open position. Specifically, interaction between the protrusions and the retention surface prevents the first member 16 and the second member 18 from becoming vertically separated along the rotational axis R of the implant 10.

Figure 8:
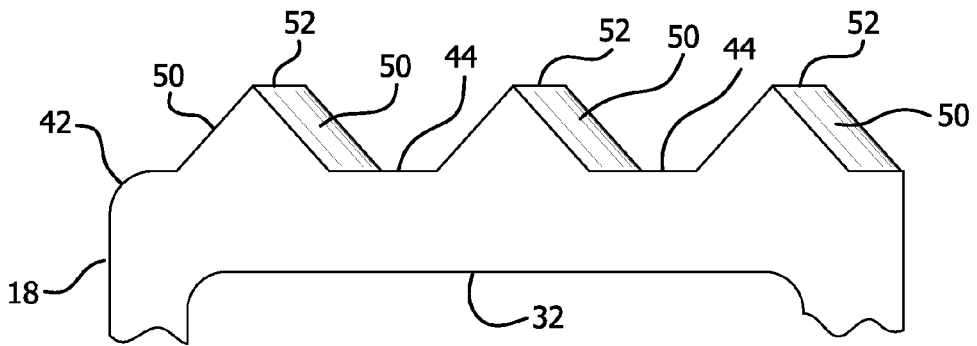
FIG. 8 is a cross-sectional view taken along the line 8-8 of FIG. 7B.
Figure 9:
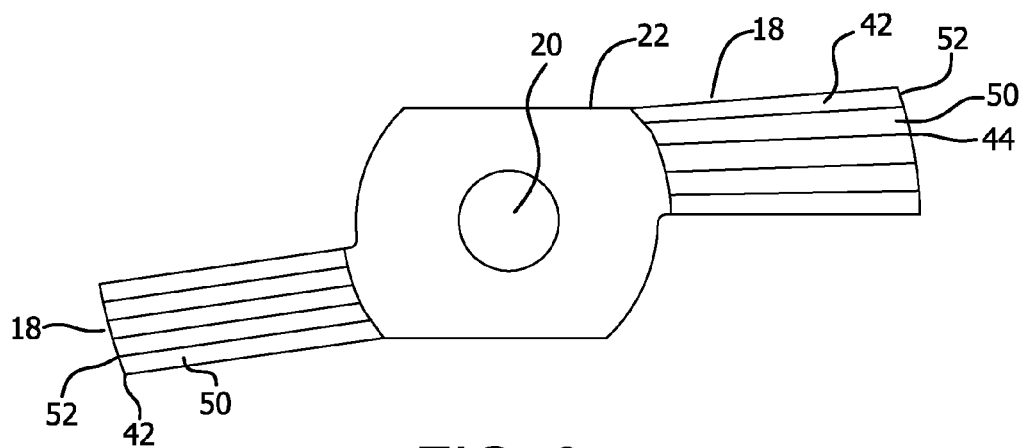
FIG. 9 is a top view of a first member of the expandable spinal implant of FIG. 7B.
Figure 10:
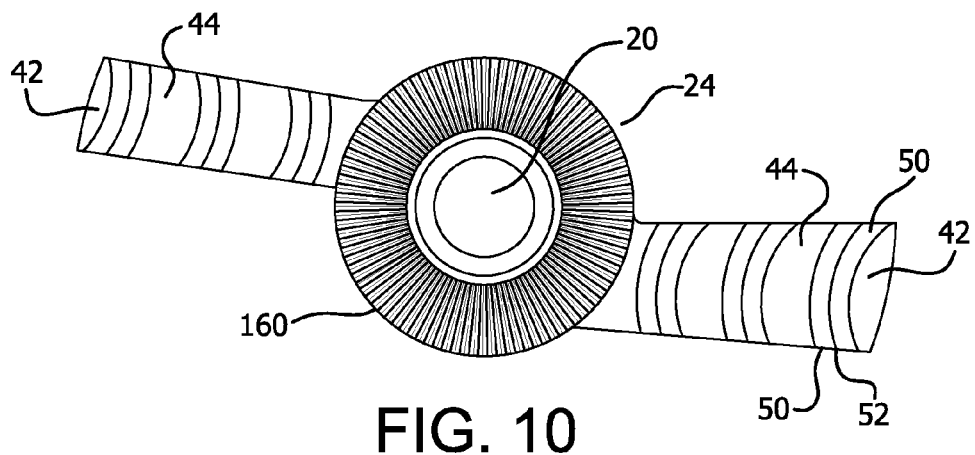
FIG. 10 is a top view of the second member of the expandable spinal implant of FIG. 7B.

To manipulate and secure implants 10 and 100 in the open position, implants 10 and 100 further include a pivot and locking mechanisms. The pivot and locking mechanism is preferably an active locking mechanism comprised of a lock aperture 164 for receiving a pin member having complimentary gearing which is mateably received by pivot gear teeth 160 on the upper surface of the first member. The upper and lower central portion surfaces may also include a detail or a resilient lip to prevent implant 10 from exceeding a maximum "X" configuration from the central portion 20 of both the first member 16 and the second member 18. FIG. 8 is a close up segment view of one section of the spinal implant 100 shown in FIG. 7B along the line 8-8. Upper surface 42 of second member 18 is shown having teeth sidewalls 50, teeth 52 and upper retention surfaces 44 which are positioned on the upper wall 32 of teeth sidewalls 50 of first member 16 may be straight and radially aligned or they may be angled or positioned diagonally or they may be any combination thereof. In other embodiments protrusions 52 and upper retention surfaces 44 slightly curved in a direction which is generally a way from central portion 20. In this regard, as shown in FIG. 10, the angle extends inwardly towards central portion 20 although it will be appreciated that the above structures 20, 52 and 44 can be substantially without any curvature, may follow a curvature which extends outwardly away from central portion 20 or may be constructed to include one or more of the above configurations and/or have those appearing on the lower surface. FIGS. 9 and 10 are first and second elongated members 16 and 18, respectively, shown with structural elements previously called out in the preceding figures starting with FIG. 4. For ease of readability previously identified structures are numbered accordingly.

An exemplary implantation of implants 10 and 100 of the present teachings within the spine 12 will now be described. Before implants 10 and 100 are inserted, the spine 12 must be prepared to receive the implant 10 by the operating surgeon. Preparation of the spine 12 involves making a small incision posteriorly within the annulus. The adjacent vertebrae 14 are distracted to return normal spacing and the intervertebral disk is removed. Once the spine 12 has been prepared, implants 10 and 100, orientated in the closed position, are inserted between the first vertebra 14a and the second vertebra 14b. To insert implants 10 or 100 in the closed position requires only a small incision in the annulus matter and only minimal distraction of the spine 12, thus maintaining the integrity of the vertebrae 14 and permitting the surgeon to make the most efficient use of operating room time. When positioned in the open orientation (FIG. 3), the spinal implant 10 or 100 stabilizes the spine 12 and facilitates the fusion of a pair of adjacent vertebrae 14.

After the implant 10 is properly installed within the spine 12 (FIG. 2), the first member 16 and the second member 18 are rotated from the closed position to the open position so that the implant 10 may provide the required support between the adjacent vertebrae 14. Rotation of the implant 10 from the closed position is effectuated by the attending surgeon using suitable operating room instrumentation. The implant 10 positioned into and is maintained in the open position through interaction between a pivot and locking gear and the cooperating geared surfaces respectively.

Rotation of the implant 10 into the open position is facilitated by the ramped teeth 50, which are ramped in the opposite direction of the expansion of the implant 10 from the closed position to the open position. Ramped teeth 50 also help maintain the implant 10 in the open position. Further, ramped teeth 50 help maintain the implant 10 in its proper position between the vertebrae 14.

Adjacent vertebrae 14 may optionally be supported by additional implants 10. The process for inserting additional implants 10 is substantially identical to the process described above for inserting a single implant 10, with the exception being that at least one additional implant 10 is inserted between other adjacent or non-adjacent vertebrae 14 during the insertion process. The use of multiple implants 10 may be advantageous as multiple implants 10 (each is separate vertebral spaces) provide additional support to the vertebrae 14 to further disperse stress loads.

The implants of the present invention may be of various different sizes to properly fit patients having spines 12 and vertebrae 14 of different sizes. The size of implant 10 and 100 (as well as others herein disclosed) may vary in numerous different ways. For example, the first elongated member 16 and the second elongated member 18 may be of various different lengths to support vertebrae 14 of different surface areas. Further, the first elongated member 16, the second elongated member 18, and the central portions 20 may be of different heights to support vertebrae 14 that are spaced at varying distances from each other.

The implant 10, may be manufactured from any biocompatible material that is suitably rigid to withstand the pressures exerted upon the implant 10 by the vertebrae 14. Examples of materials that may be used to manufacture the implant 10 include, but are not limited to, PEEK (polyether ether ketone), titanium and allograft bone. PEEK is not traditionally a shape memory polymer; however, recent advances in processing have allowed shape memory behavior in PEEK with mechanical activation. This technology has expanded to applications in orthopedic surgery. As shown throughout the drawings, the first member 16, and the second member 18, each preferably comprise a single unitary structure. With initial reference to FIG. 11 an exemplary spinal implant constructed in accordance with the present teachings is illustrated and generally identified at reference number 1000. The spinal implant 1000 is shown operatively associated with a human spinal column 12. More specifically, the spinal implant 1000 is shown positioned between a first vertebra 14a and a second vertebra 14b to stabilize the spine 12.

Figure 11:
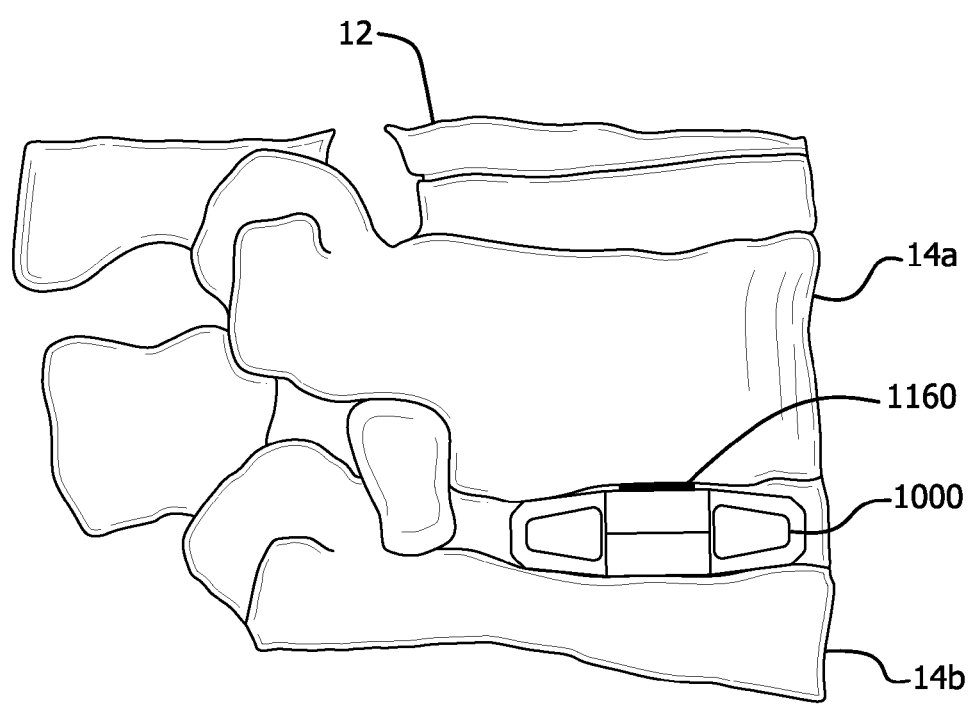
FIG. 11 is a side view of another embodiment of an expandable spinal implant constructed in accordance with the present teachings, the expandable spinal implant shown operatively positioned between vertebral bodies of a human spine.
Figure 12:
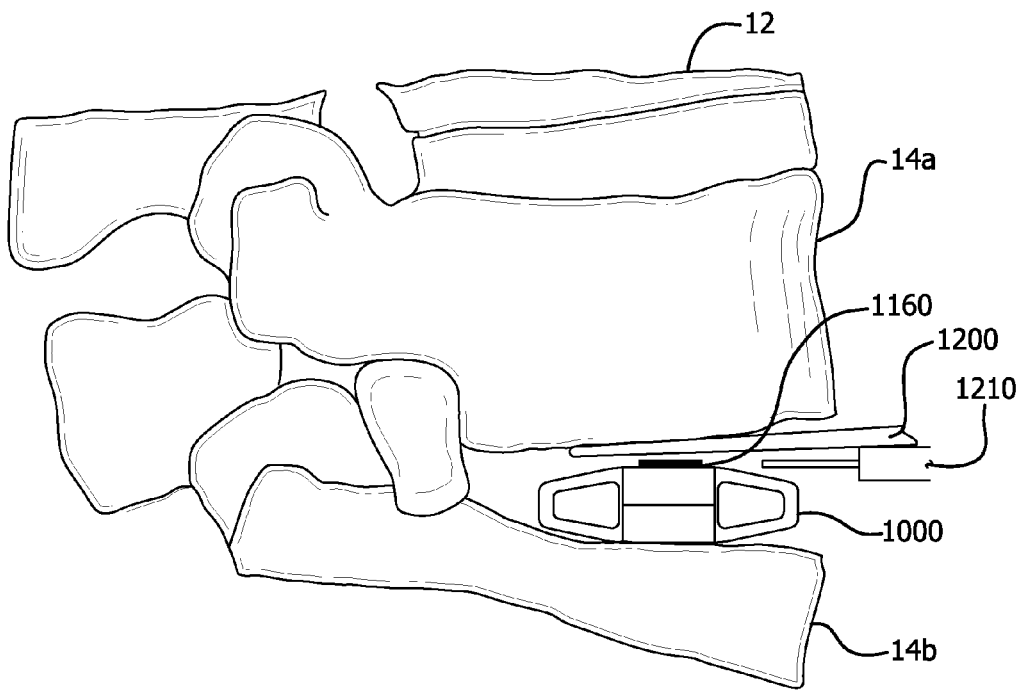
FIG. 12 is a side view of the embodiment of the expandable spinal implant of FIG. 11, the expandable spinal implant shown in combination with associated spinal expansion and insertion tools to facilitate into the spine and adjustment therein.

With continued reference to the environmental views of FIGS. 11 and 12 and additional reference to FIGS. 13 through 17, the spinal implant 1000 of the present teachings will be addressed in detail. As previously noted, similar structures and elements in other embodiments disclosed herein will share like reference numbers in the description and the Figures. For sake of readability, reference to the previous description of the preceeding figures is incorporated herein.

The spinal implant 1000 is illustrated to generally include a first member or first elongated member 16 and a second member or second elongated member 18. As will become more apparent from the descriptions above and below, the first elongated member 16 and the second elongated member 18 are completely separate members and are coupled to one another for relative movement between a closed position or orientation and an expanded position or orientation via pivot and locking gear 1160. As will be appreciated more fully below, the closed orientation facilitates insertion of the spinal implant 1000 within the spine 12 through a small incision, while the expanded or open orientation disperses the load on the adjacent end plates.

Figure 13:
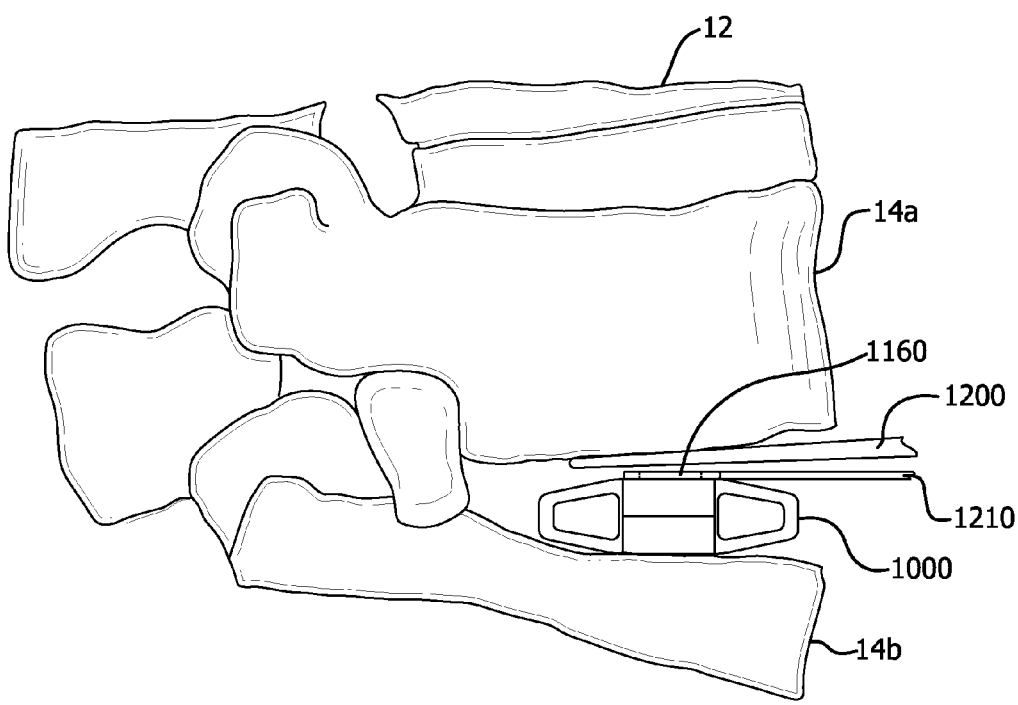
FIG. 13 is a side view of the embodiment of the expandable spinal implant of FIGS. 11 and 12, the expandable spinal implant shown in cooperation with associated spinal expansion and insertion tools to facilitate into the spine and adjustment therein.

Referring to FIGS. 12 and 13, spinal implant 1000 is shown with associated insertion and adjustment tools including spinal expansion apparatus 1200 and adjustment tool 1210. Spinal expansion apparatus 1200 is positioned within the spinal space and provides temporary expansion of the spinal space to facilitate insertion of spinal implant 1200 and operation of adjustment tool 1210 thereby causing spinal implant 1000 to move between a closed position or orientation and an expanded position or orientation.

Figure 14A:
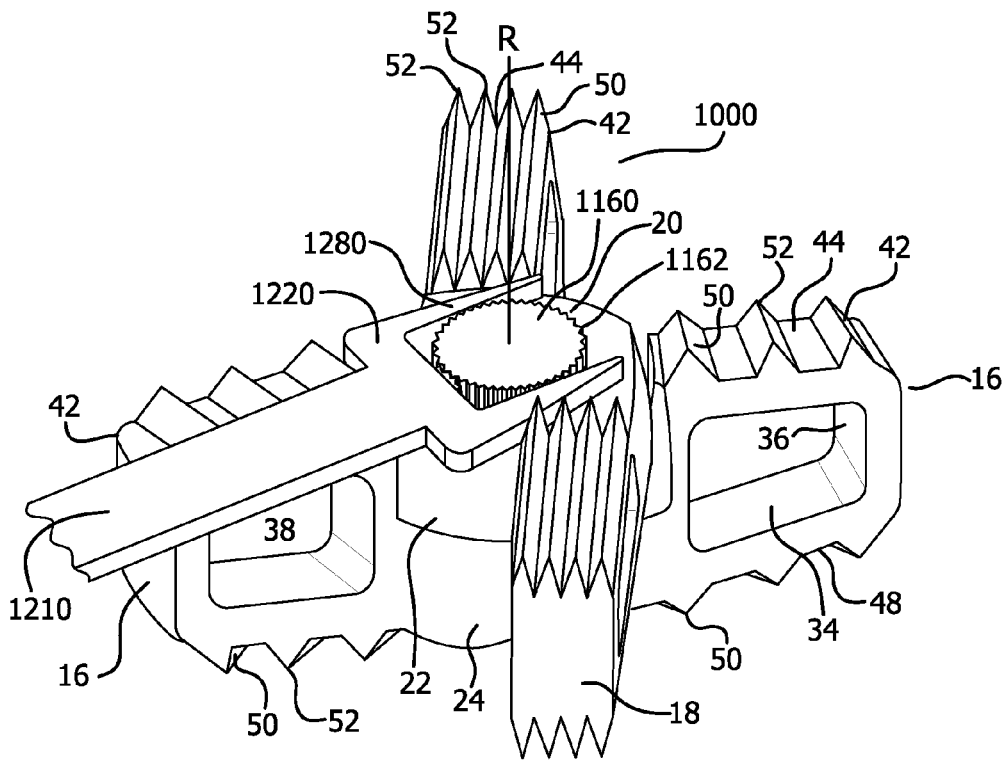
FIG. 14A is a perspective view of an expandable spinal implant similar to that shown in FIGS. 11 through 13 with an exemplary adjustment tool, shown removed from the spine for purposes of illustration.
Figure 14B:
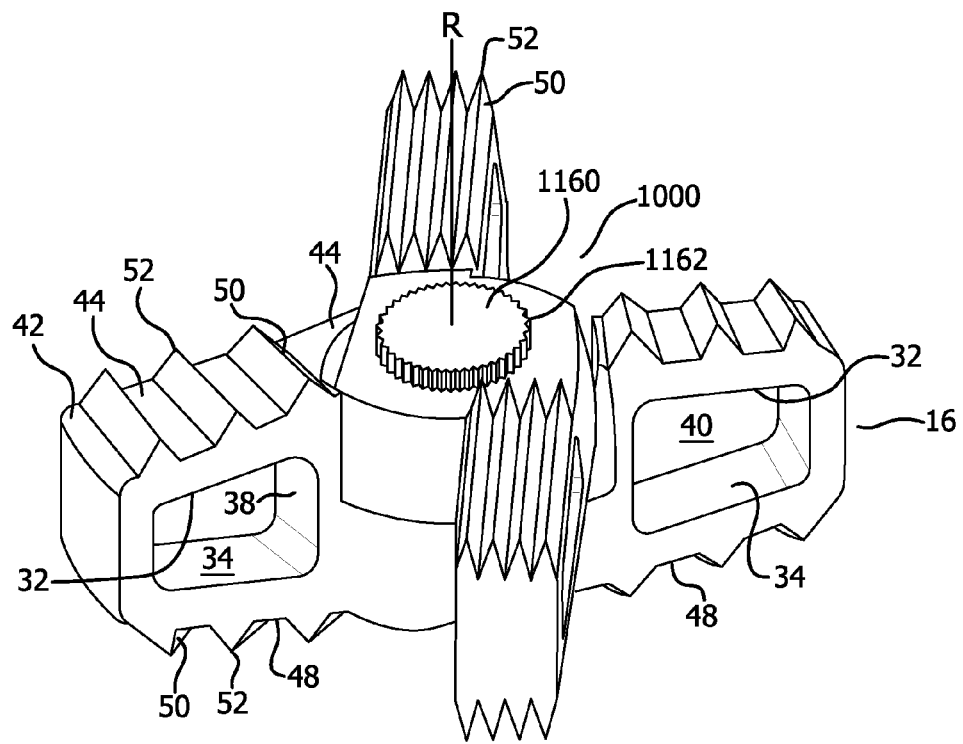
FIG. 14B is a perspective view of an expandable spinal implant similar to that shown in FIGS. 11 through 13, and shown removed from the spine for purposes of illustration.

With particular reference to FIGS. 14A and 14B, the first elongated member 16 and the second elongated member 18 are shown coupled together in the open position. In the open position the first arm 28 of the first elongated member 16 is positioned apart from and in a non-parallel relationship to the second arm 30 of the second elongated member 18. Likewise, the second arm 30 of the first member 16 is positioned apart from and in a non-parallel relationship to the first arm 28 of the second elongated member 18. Generally, in the open position the first member 16 and the second member 18 are rotated such that the arms 28 and 30 of the first member 16 and the arms 28 and 30 of the second member 18 have an overall configuration approximating that of an "X". This "X" shaped configuration provides the implant 10 with a great deal of strength to support the vertebrae 14 of the spine 12.

The first elongated member 16 and the second elongated member 18 each further comprise a plurality of protrusions and a plurality cooperating of recesses 54. The protrusions extend from the upper face 42 and the recesses are located within the outer surface 24 of the central portion 20. The recesses have a sidewall and a retention surface 58. As the first and second elongated members 16 and 18 are rotated from the closed position to the open position, the protrusions rotate within the recesses such that each protrusion contacts both the sidewall and the retention surface.

As seen most clearly in FIG. 14A and FIG. 14B, cooperation between the protrusions of the first elongated member 16 and the recesses of the second elongated member 18, as well as cooperation between the protrusions of the second elongated member 18 and the recesses of the first elongated member 16, ensures that the first elongated member 16 stays coupled to the second elongated member 18 when the implant 1000 is in the open position. Specifically, interaction between the protrusions 52 and the retention surface prevents the first member 16 and the second member 18 from becoming vertically separated along the rotational axis R of the implant 1000.

Pivot and locking gear 1160 is operatively connected to threaded and/or geared assemblies having complimentary mating structures (not shown) which engage one or both first and second members 16 and 18 respectively so as to facilitate movement of the members from the closed to the open positions and vice versa. In this manner, pivot and locking gear teeth 1162 may be rotated by the appropriate tool in a clockwise or counter-clockwise direction and the internally positioned drive teeth 1174 (shown in FIGS. 18 and 19) which are operatively connected to complimentary threaded and/or geared assemblies situated at or near upper and/or lower surfaces of central portion 20 will result in movement of first member 16 and second member 18 relative to one another from the closed to the open position and vice versa.

Figure 15:
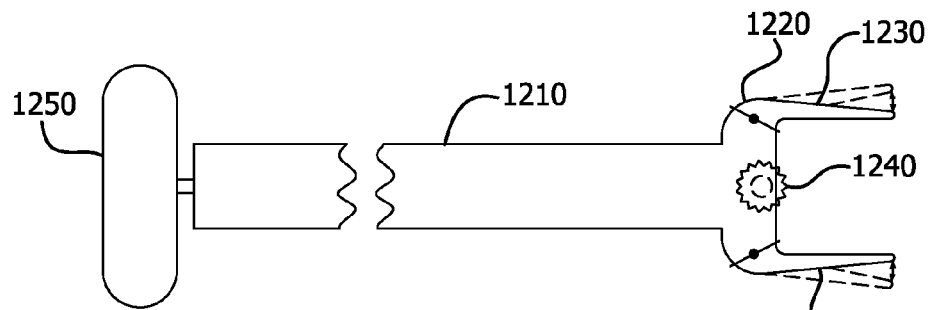
FIG. 15 is a top plan view of an exemplary adjustment tool for use with an embodiment of an expandable spinal implant according to the present invention.
Figure 16:
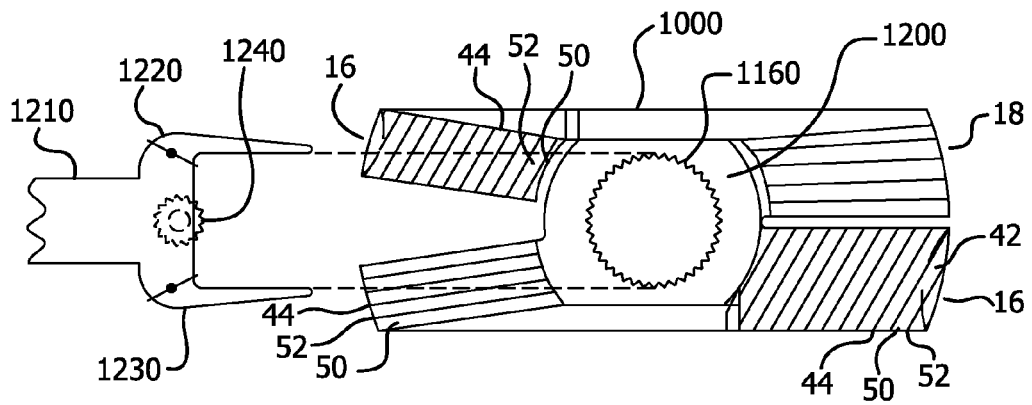
FIG. 16 is a top plan view of the exemplary adjustment tool for used in FIG. 15 in combination with an embodiment of an expandable spinal implant according to the present invention.
Figure 17:
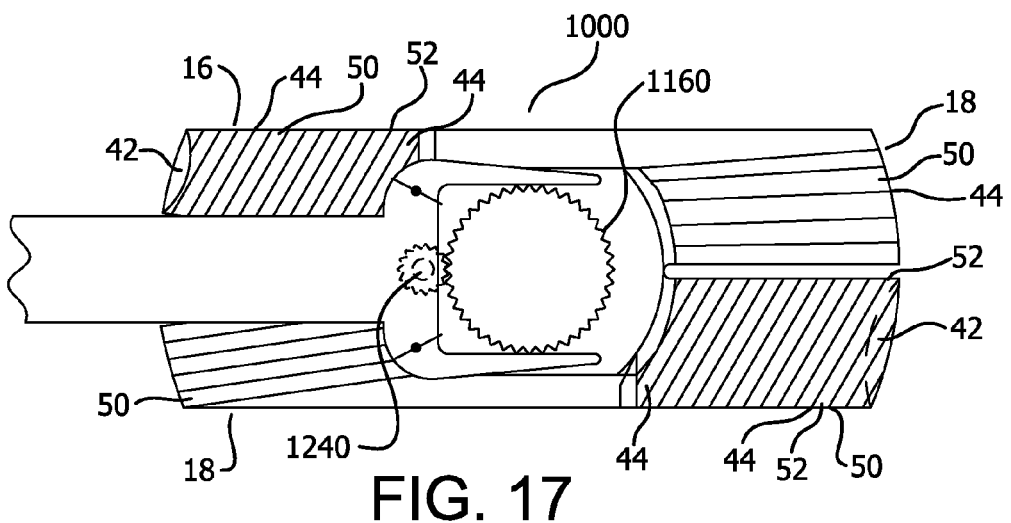
FIG. 17 is a top plan view of the exemplary adjustment tool for use of FIG. 15 in operative communication with an embodiment of a expandable spinal implant of the present invention.

In FIG. 14A, there is shown one embodiment of a form of adjustment tool 1210 in operational contact with pivot and locking gear 1160 of spinal implant 1000. In the embodiment shown, adjustment tool 1210 includes adjustment tool head 1220 and a pair of moveable adjustment tool arms 1230. Positioned within adjustment tool head 1220 and generally centrally positioned between tool arms 1230 will be a drive gear 1240 (as shown in FIGS. 15 through 17) for rotating pivot and locking gear 1160. It will be appreciated that the tool arms 1230 may further include mechanisms for selectively securely gripping and releasing pivot gear 1160. In this regard it will be understood that implant 1000 will be detachably mounted to adjustment tool 1210 so as to permit secure and accurate placement of the implant within the spinal space and release of implant 1000 upon proper placement and positioning.

To manipulate and secure the implant 1000 in the open position, the implant 1000 further includes a pivot and locking mechanism. In the embodiment shown, the pivot and locking mechanism is preferably an active locking mechanism comprised of an aperture for mateably receiving pivot and locking gear 1160 on the upper surface of and internally within the central portion 20. The upper and lower central portion surfaces may also include a detail or stop to prevent implant 10 from exceeding a maximum "X" configuration from the central portion 20 of both the first member 16 and the second member 18.

Referring now to FIG. 15, there is shown an exemplary adjustment tool used with the spinal implant 1000 of the present invention. Adjustment tool 1210 is shown having adjustment tool head 1220 and adjustment tool arms 1230. Positioned generally centrally between adjustment tool arms 1230 is driving gear 1240 which is operatively connected to drive head 1250. Internal gearing linkages between driving gear 1240 drive head 1250 and for operatively securely gripping and releasing pivot and locking gear 1160 are well known and are outside of the scope of the present invention. It will be appreciated that the embodiment shown is just one example of an adjustment tool which may be useful in connection with the spinal implant 1000 of the present invention and that such adjustment tool 1210 may take other forms or include other features not shown or described herein. The key feature of any such tool will be the ability to securely detachably grip, position and release the implant and to operatively engage pivot and locking gear 1160 and more specifically pivot gear teeth 1162 of pivot and locking gear 1160.

FIGS. 16 and 17 show adjustment tool head 1220 positioned to be operatively engaged with an exemplary embodiment of spinal implant 1000. As can be seen from the Figures, first elongated member 16 and second elongated member 18 include structures and elements previously identified by the within like referenced numbers. It will be understood that the arrangement and configuration of teeth sidewalls 50, protrusions 52, and retention surfaces 44 of the first and second members may be both radially or circumferentially arranged on spinal implant 1000. Alternatively, teeth sidewalls 50, protrusions 52, and retention surfaces 44 may take other forms or other configurations and may be all arranged radially or circumferentially and may be arranged diagonally as situations or preferences may dictate including any suitable combinations thereof.

FIG. 17 provides a close-up view of adjustment tool head 1220 driving gear 1240 in operative engagement with pivot and locking gear 1160. As previously noted similar structures and elements have like reference numerals. It will be understood that as drive gear 1240 moves in a rotational direction, drive gear teeth 1260 engage pivot gear teeth 1162 of pivot gear 1160 causing internally coupled first and second members to move relative to one another from a closed configuration to the expanded or open "X"-shaped configuration. Importantly, it will also be understood that pivot and locking gear 1160 also provides an internal locking mechanism to keep the first and second members the expanded or open "X"-shaped configuration and may further include a semi-elastic detent, annular rim or other detail including biocompatible adhesive materials and compressive or snap-fitments which facilitate permanent or semi-permanent fixing of spinal insert 1000 in the preferred position to support the vertebral segments most effectively.

FIGS. 18 and 19 are side and front end views of one embodiment of the pivot and locking gear 1160 of the type suitable for use with spinal implant 1000. As can be seen from FIGS. 18 and 19, pivot and locking gear 1160 includes at or near first end 1164, annularly arranged pivot and locking gear teeth 1162, and a second end 1166. Second end 1166 may be separated from pivot and locking gear teeth 1162 by spacing member 1168 for extending into central portion 20. Positioned on or near spacing member 1168 is annular ring 1170 which may be adapted for and received by a snap fit or other compressive fitment within central portion 20 and for securing and locking pivot and locking gear 1160 in the expanded or open "X"-shaped configuration. Positioned at or near pivot gear lower surface 1172 are pivot gear drive teeth 1174 which are mateably geared an internal complementary gear arrangement (not shown) within central portion 20 coupled to first and second members. Securing and locking implant 1000 in the expanded or open configuration may be accomplished, for example, by simply engaging the compressive fitment by downward pressure on pivot and locking gear 1160, by rotation of pivot and locking gear 1160 to a depth beyond the annular ring 1170 to engage the snap fit, or by the use of biocompatible adhesive materials as well as by other known equivalent mechanical structures and methods.

FIG. 20 and FIG. 21 are side and front views respectively, of an embodiment of a pivot and locking gear 1600 adapted for use in other embodiments of the spinal implant of the present invention. Pivot and locking gear 1600 includes first end 202, head member 204, spacing member 206, axial gear 208 and second end 210. It will be understood that other types of gearing arrangements may be used for operatively engaging the internally disposed complementary gear within the central portion of the implants disclosed herein. Positioned within the body of head member 204 is drive socket 212 which may be operatively engaged with the appropriate surgical tool when pivot and locking gear 1600 placed within the body of spinal implant of the types depicted in spinal implants 10, 100, and/or 1000.

It will be further understood that the pivot and locking gear 1600 depicted may take other forms and may include other features. The pivot and locking gear 1600 can be deployed using a driver or similar tool that inserts pivot and locking gear 1600 into pivot and lock aperture 164 of central portion 20 and operated to engage and to rotate the pivot and locking gear teeth 160Q, thereby causing pivot and locking gear 1600 to advance into pivot and lock aperture 164, cause the first and second elongated members to rotate with respect to each other and positively secure spinal implants 10, 100 and 1000 in the open orientation. In this regard, pivot and locking gear 1600 includes a head formation for receiving a tool for rotating the first and second members from the closed orientation to the open orientation after implantation.

It will also be understood that in certain embodiments of the present invention, pivot and locking gear 1600 may be preassembled within central portion 20 in order to reduce the number of separate component parts during implantation.

As in the case with the pivot and locking gear of FIGS. 18 and 19, it will also be understood that pivot and locking gear 1600 also provides an internal locking mechanism to keep the first and second members the expanded or open "X"-shaped configuration. In this regard, pivot and locking gear 1600 may further include a semi-elastic detent, annular rim or other detail including compressive or snap-fitments as well as biocompatible adhesives which facilitate permanent or semi-permanent fixing the spinal insert 10 and 100 in the preferred position to support the vertebral segments most effectively.

Figures 22, 23:
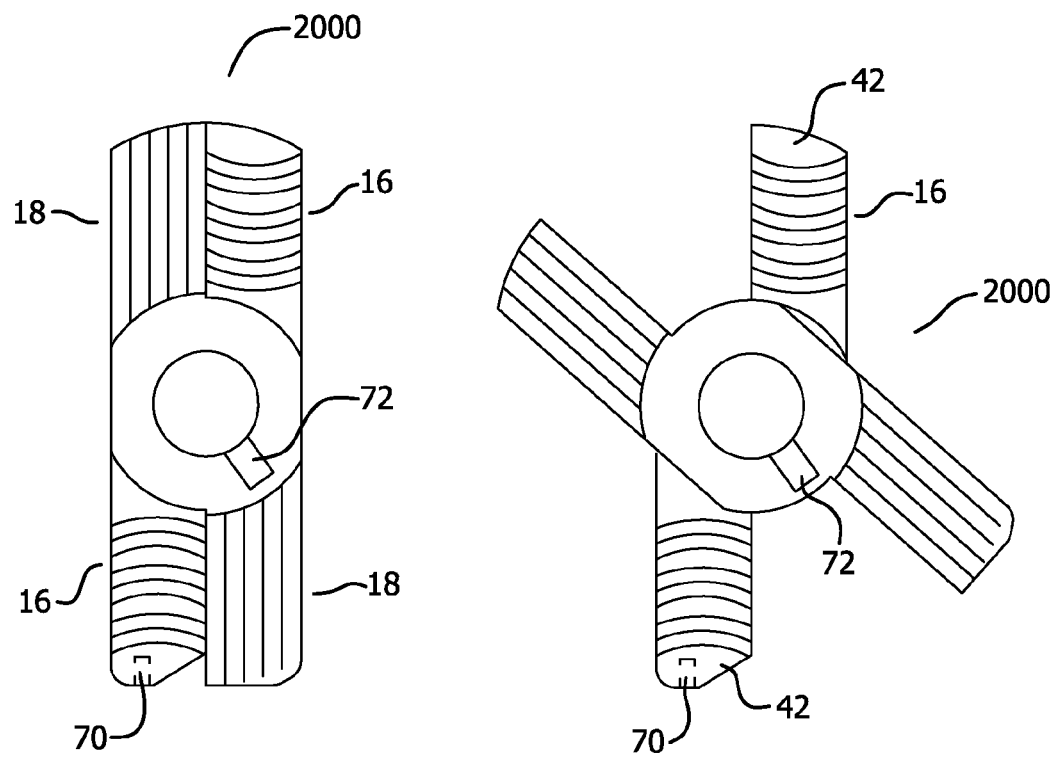
FIG. 22 is a top perspective view of another embodiment expandable spinal implant shown in the closed position outside the spinal space for purposes of illustration.
FIG. 23 is a top perspective view of another embodiment expandable spinal implant shown in the open position outside the spinal space for purposes of illustration.
Figure 24:
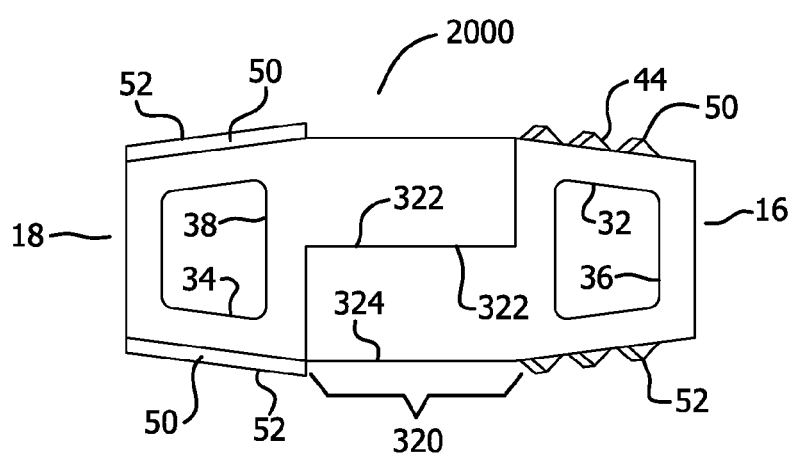
FIG. 24 is a side view of the expandable spinal implant of FIG. 22 shown in the closed position outside the spinal space for purposes of illustration.

In FIGS. 22, 23 and 24, another exemplary embodiment of the spinal implant 2000 of the present invention is shown. Similar structures and elements in other embodiments disclosed herein will share like reference numbers in the description and the Figures. The elongated members 16 and 18 are illustrated coupled together in the closed position in FIG. 22 and in the open position in FIG. 23. In the closed position, the first arm 28 of the first elongated member 16 is positioned roughly parallel to and adjacent to the second arm 30 of the second elongated member 18. The second arm 30 of the first member 16 is positioned parallel to and adjacent to the first arm 28 of the second elongated member 18. At one end of first member 16 is contact surface 80 for engagement with an associated tool and which provides a temporary anchoring surface to facilitate movement of first member 16 relative to second member 18. Positioning the arms 28 and 30 of the first elongated member 16 roughly parallel to and adjacent to the arms 28 and 30 of the second elongated member 18 provides the implant 10 with a slim and compact profile that permits the implant 10 to be easily inserted within the spine 12 requiring only a minimal disruption of the vertebrae 14 and the annulus (not shown).

Within elongated member 16, at or near a distal end of the first arm 28 is holding pin recess 70 and tool engaging surface 43 which is adapted to be engaged by a lever arm 73 of insertion and rotation tool assembly as shown more clearly in FIGS. 25 and 26. Within central portion 20 of spinal implant 2000, is recess 72 for receiving a screw or a pin member (not shown) which is inserted into recess 72 to maintain spinal insert 2000 in the open or X-shaped configuration after introduction into the vertebral space.

The screw or a pin member can be, for example, a fastener, such as screw or bolt, which engages pin recess 72 which is positioned in the respective central portions 20 of the first and second members 16, 18 to prevent rotation therebetween once in the open configuration. The pin member can include a head or a stepped shank which is received into recess 72 of central portions 20 of the first and second members. The pin member can include a head formation for receiving a tool for locking the first and second members in the open orientation after implantation.

FIG. 24 depicts a side view of the spinal implant 2000 as shown in FIGS. 22 and 23. The first elongated member 16 and the second elongated member 18 are separately formed and are connected at approximately a mid-line 322 and each further comprise a plurality of protrusions and a plurality of cooperating of recesses (not shown). The protrusions extend from the upper face 42 and the recesses are located within the outer surface 324 of the central portion 320. The recesses have sidewalls and retention surfaces.

FIGS. 25 and 26 show one form of an insertion and rotation tool 310 used in connection with an exemplary spinal implant 2000 as depicted in FIGS. 22, 23 and 24. Tool 310 includes at one end, lever trigger arm 314, handle 316 and stabilizing pin manipulator 318. At the opposite end, there is positioned lever arm 71 which is operatively connected to lever trigger arm 314 and stabilizing pin rod 78 attached to stabilizing pin rod 76. Lever trigger arm 314 is connected via linkage to lever arm 71 via upper chamber 320. Stabilizing pin manipulator 318 is operatively connected to stabilizing pin 78 and stabilizing pin rod 76 via lower chamber 322.

Spinal implant 2000 may be detachably connected to tool 310 at stabilizing recess 80 via stabilizing pin 76 and the stabilizing pin rod 78. Upon insertion of spinal implant 2000 into the spinal space, holding pin recess 70 on first elongated member 16 is engaged by tool engaging surface 43 of lever arm 71. As lever trigger arm 314 is moved rearwardly in the direction of handle 316, lever arm 71 moves in an arc like path and engages contact surface 82 causing spinal implant 2000 to move from the closed position to the open expanded position. The central portion 2020 of the second elongated member 18 rotates relative to the first elongated member 16 and locking pin bore 74 within central portion 320 moves into position to allow locking pin 80 to enter into locking pin bore 74 via upper chamber bore. Upon proper expansion of spinal implant 2000, stabilizing pin rod 78 and stabilizing pin 76 may be retracted, thereby permitting removal of tool 310.

It will be appreciated that implants 10, 100, 1000 and 2000 are merely exemplary illustrations, such that various features of exemplary implant 10 can be incorporated in exemplary implant 100, features of exemplary implant 10 can be incorporated in exemplary implant 1000 and features of exemplary implant 10 can be incorporated in exemplary implant 2000, etc. and vice versa.

The description of the invention is merely exemplary in nature and, thus, variations that do not depart from the gist of the present teachings are intended to be within the scope of the present teachings. Such variations are not to be regarded as a departure from the spirit and scope of the present teachings.

What is claimed is:

1. An expandable spinal implant comprising:
a first member having first and second arms and a first central portion between the first and second arms;
a second member separate from the first member, the second member having first and second arms and a second central portion between the first and second arms, the central portion of the first member being operatively joined to and rotatably coupled to the central portion of the second member about a rotation axis substantially perpendicular to the first and second central portions between a closed position to insert the implant into a spine and an expanded position to provide structural support to the spine, the first and second members are coupled to each other such that the first and second arms of the first member alternate with the first and second arms of the second member; and
a pivot and locking gear configured to deployably pivot and lock the expandable implant from the closed position to the expanded position, wherein the first and second central portions include a bore to receive the pivot and locking gear.

2. The expandable spinal implant of claim 1, wherein the first and second arms of the first member are generally parallel and spaced apart relative to one another and the first and second arms of the second member are generally parallel and spaced apart relative to one another.

3. The expandable spinal implant of claim 1, wherein the first arm of the first member is generally parallel to and adjacent the second arm of the second member in the closed position.

4. The expandable spinal implant of claim 1, wherein at least one of the first and second arms of at least one of the first and second members defines a window to facilitate bone ingrowth.

5. The expandable implant of claim 1, wherein the pivot and locking gear is substantially perpendicular to the first and second members and operatively engages at least one of the first and second members.

6. The expandable spinal implant of claim 5, wherein the pivot and locking gear is a threaded assembly which engages respective aperture and gear teeth of at least one of the first and second central portions of the first and second members.

7. An expandable spinal implant comprising:
a first member having first and second arms and a first member central portion between the first and second arms;
a second member completely separate from the first member, the second member having first and second arms and a second member central portion between the first and second arms wherein the central portion of the second member and central portion of the first member comprise a combined central portion;
wherein the central portion of the first member is rotatably engaged with the central portion of the second member about a common rotation axis substantially perpendicular to the first member and second member central portions by a pivot and locking gear to facilitate movement between a closed position to inserting the implant into a spine and an expanded position to provide structural support to the spine, the first and second members coupled to each other such that the first and second arms of the first member alternate with the first and second arms of the second member;
wherein each of the first and second arms of the first member and the first and second arms of the second member defines a plurality of teeth, the teeth being radially oriented when the first and second members are rotated to the expanded position.

8. The expandable spinal implant of claim 7, wherein the first and second members are substantially identical.

9. An expandable spinal implant having a rotational axis comprising:
a first member having a first member central portion and first and second arms extending from the central portion of the first member;
a second member having a second member central portion and first and second arms extending from the central portion of the second member,
a pivot and locking gear substantially parallel to the rotational axis of the first and second members, the pivot and locking gear being operatively engaged with the central portion of the second member and the central portion of the first member to facilitate crosswise rotation about a rotational axis between a closed orientation to insert into a spine and an expanded orientation to provide structural support to the spine; and
the pivot and locking gear further comprising a lock to arrest relative movement between the first member and the second member, the lock selected from the group consisting of annular rings, including compressive or snap-fitments and biocompatible adhesives, the pivot and locking gear being manually operable to engage the first member with the second member in the expanded orientation, and wherein the pivot and locking gear comprises a threaded fastener.

10. An expandable spinal implant comprising:
a first member having a first member central portion and first and second arms extending from the first member central portion of the first member;
a second member having a second member central portion and first and second arms extending from the second member central portion of the second member, the central portion of the second member coupled to the central portion of the first member comprising a combined central portion to rotate about a rotation axis between a closed orientation to insertion into a spine and an expanded orientation to provide structural support to the spine and at least one aperture positioned within at least one of the first or second member central portions;
a pivot and locking gear to insert into the at least one aperture, the pivot and locking gear comprising a head segment and a threaded segment wherein the threaded segment further comprises a lock to arresting relative movement between the first member and the second member, the lock being operable to lock the first member and the second member relative to one another in a fixed position; and
wherein each of the first and second arms of the first member and the first and second arms of the second member define a plurality of teeth, the teeth being concentrically oriented when the first and second members are rotated into the expanded position.

11. An expandable spinal implant having a rotational axis comprising:
a first member having a first member central portion and first and second arms extending from the central portion of the first member;
a second member having a second member central portion and first and second arms extending from the central portion of the second member,
the first member central portion and the second member central portion form a combined central portion, a pivot and locking gear substantially perpendicular to the rotational axis of the first and second members, the pivot and locking gear engage the second central portion of the second member and the first central portion of the first member to facilitate crosswise rotation about the rotational axis between a closed orientation to insert into a spine and an expanded orientation provide structural support to the spine; and the pivot and locking gear including a head segment and a threaded segment, the pivot and locking gear operable to rotatably engage the first member and the second member, relative to one another and to arrest relative movement between the first member and the second member wherein the threaded segment further comprises a lock to arrest relative movement selected from the group consisting of, annular rings, including compressive or snap-fitments and biocompatible adhesives;

and wherein each of the first and second arms of the first member and the first and second arms of the second member defines a plurality of teeth, the teeth being oriented substantially radially, concentrically or a combination of the two when the first and second members are rotated in to the expanded position.

* * * * *